United States Patent [19]

Clinton, deceased et al.

[11] 4,316,988

[45] Feb. 23, 1982

[54] N-ALKYLDIPHENYLAMINES

[75] Inventors: Albert J. Clinton, deceased, late of Marion, Ind., by Thomas L. Plimpton, administrator; George O. P. O'Doherty, Greenfield, Ind.

[73] Assignee: Eli Lilly and Company, Indianapolis, Ind.

[21] Appl. No.: 219,791

[22] Filed: Dec. 24, 1980

Related U.S. Application Data

[63] Continuation-in-part of Ser. No. 706,023, Jul. 21, 1976, abandoned.

[51] Int. Cl.$^3$ .................... C07C 87/54; C07C 87/60; C07C 87/62
[52] U.S. Cl. ................................. 564/433; 564/435; 424/330
[58] Field of Search ............... 564/433, 435, 406, 305; 424/330

[56] References Cited

U.S. PATENT DOCUMENTS

| | | | |
|---|---|---|---|
| 2,212,825 | 8/1940 | Daudt | 260/571 |
| 4,117,167 | 9/1978 | Barlow et al. | 424/330 |
| 4,187,318 | 2/1980 | Dreikorn | 424/330 |
| 4,215,145 | 7/1980 | Grantham | 424/324 |

FOREIGN PATENT DOCUMENTS

| | | | |
|---|---|---|---|
| 846205 | 9/1976 | Belgium | 424/330 |
| 3259 | 8/1979 | European Pat. Off. | 424/330 |
| 868165 | 5/1961 | United Kingdom | 564/406 |

OTHER PUBLICATIONS

Patat et al., "J. Chem. Soc.", pp. 1035–1038, (1959).
Agricultural Chem., Book 1, Insecticides, 1977 Revision, by W. T. Thompson, (Thompson Publications, Fresno, CA 1977), pp. 76–77.

*Primary Examiner*—John Doll
*Attorney, Agent, or Firm*—Kathleen R. S. Page; Arthur R. Whale

[57] ABSTRACT

A series of new diphenylamines have small alkyl substituents on the amino nitrogen and are useful as intermediates for the preparation of rodenticidal diphenylamines. One phenyl ring has 2,4-dinitro-6-trifluoromethyl substitution, and the other is substituted with no more than one methyl or trifluoromethyl group. The invention is particularly directed to N-alkyl-2,4-dinitro-3'-6-bis(trifluoromethyl)diphenylamines, which are additionally useful as insecticides and arachnicides.

3 Claims, No Drawings

N-ALKYLDIPHENYLAMINES

CROSS-REFERENCE TO RELATED APPLICATION

This is a continuation-in-part of copending application Ser. No. 706,023, filed July 21, 1976 now abandoned.

SUMMARY OF THE INVENTION

The present invention provides a series of new compounds of the formula

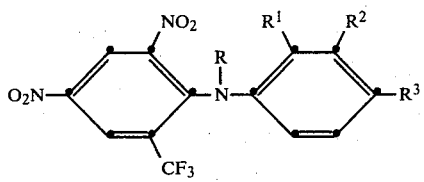

wherein
R represents methyl, ethyl or propyl;
$R^1$ and $R^2$ independently represent hydrogen, methyl or trifluoromethyl;
$R^3$ represents hydrogen or methyl; provided that no more than one of $R^1$, $R^2$ and $R^3$ represents a group other than hydrogen.

DETAILED DESCRIPTION OF THE INVENTION

All of the compounds described in this document will be named as diphenylamines for the sake of consistency, even though the rules of nomenclature might call for some compounds to be named otherwise.

All percentages and parts described hereafter refer to percentages and parts by weight, and all temperatures are on the Celsius scale.

The following exemplary compounds are mentioned only to assure that the reader fully understands the invention.

N,2-dimethyl-2',4'-dinitro-6'-trifluoromethyldiphenylamine

N-ethyl-3-methyl-2',4'-dinitro-6'-trifluoromethyldiphenylamine 4-methyl-2',4'-dinitro-N-propyl-6'-trifluoromethyldiphenylamine 2-methyl-2',4'-dinitro-N-propyl-6'-trifluoromethyldiphenylamine 2,4-dinitro-N-propyl-3',6-bis(trifluoromethyl)diphenylamine N-ethyl-2,4-dinitro-2',6-bis(trifluoromethyl)diphenylamine 3-methyl-2',4'-dinitro-N-propyl-6'-trifluoromethyldiphenylamine N-ethyl-4-methyl-2',4'-dinitro-6'-trifluoromethyldiphenylamine A preferred compound of this invention is N-methyl-2,4-dinitro-3',6-bis(trifluoromethyl)diphenylamine.

The compounds of this invention are made by the following process.

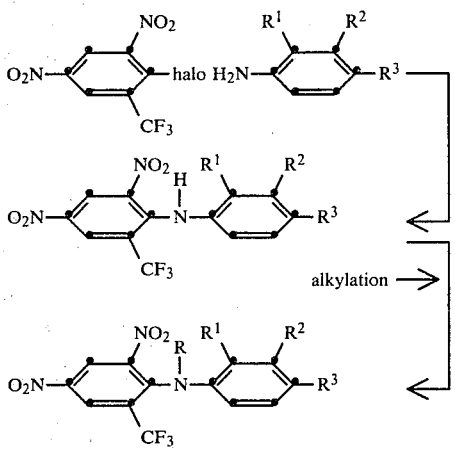

In the above formula, the term "halo" refers to any of the four common halogen atoms, of which chlorine and fluorine are preferred and chlorine is usually the most convenient.

The individual steps of the above process are not extraordinary in organic chemistry, and are conducted as a skilled organic chemist would expect. The coupling reactions which join the aniline and benzotrifluoride rings are more readily carried out at relatively low temperatures in the range of $-20°$ to $10°$ in dimethylformamide in the presence of sodium hydride. Other media are likewise useful. The reactions may be carried out, for example, in alkanols such as ethanol, in which solvents the reaction temperature may be higher, in the range of $10°$ to $25°$. Other solvents, including ketones such as acetone and methyl ethyl ketone and ethers including diethyl ether and tetrahydrofuran, are satisfactory reaction solvents.

In general, a strong base is needed to serve as acid scavenger. Sodium hydride, as mentioned above, is generally the most useful base, but other bases including inorganic bases such as sodium hydroxide and sodium carbonate, and organic tertiary amines such as pyridine and triethylamine, as well as a simple excess of the aniline starting compound, may be used.

N-Alkylation of the diphenylamines is performed with reagents such as a dialkyl sulfate or an alkyl halide in the presence of a base. When a dialkyl sulfate is used, the preferred reaction solvent is acetone. Other solvents, such as tetrahydrofuran, dioxane and diethyl ether, are also useful, as are alkanes such as hexane and octane. Dimethylformamide is the preferred solvent for alkylations with alkyl halides, although acetone is also excellent. Other solvents as described above may be used.

The preferred bases for use in the alkylation reactions are those which have a dehydrating effect, particularly sodium carbonate. However, other inorganic bases, such as the alkali metal carbonates, bicarbonates and hydroxides, can be used, as can the alkali metal hydrides.

The amount of base used depends upon the reaction temperature. The higher the reaction temperature in the alkylation step, the greater excess of base is needed. When the reaction temperature is approximately ambient, a small excess of base should be used, such as 2 moles of base per mole of diphenylamine. When very high reaction temperatures such as 100° are used, a large excess of base should be used, in the range of 10-fold.

It will be recognized that it is important to avoid contamination of the alkylation reaction mixture with water.

In general, alkylations with dialkyl sulfates are best performed at about 80°, although temperatures from approximately room temperature to the reflux temperature may be used. Conditions close to room temperature, such as from 20° to 35°, are preferred for alkyl halide alkylations, but elevated temperatures up even to as high as 150° may be used.

The starting substituted anilines and phenyl halides are readily obtained by methods which are commonly known in the chemical literature. For the convenience of the chemist, the following references discussing the synthesis of substituted anilines are mentioned. Finger et al., *J. Am. Chem. Soc.* 81, 94–101 (1959); McBee et al., *J. Am. Chem. Soc.* 73, 3932–34 (1951); Finger et al., *J. Am. Chem. Soc.* 73, 145–49 (1951); Bachman et al., *J. Am. Chem. Soc.* 69, 2022–25 (1947); Dains, *J. Am. Chem. Soc.* 52, 1573 (1930).

The trifluoromethyl-substituted anilines are best prepared, as chemists will recognize, by first obtaining a carboxylic acid-substituted aniline having the acid groups at the locations of the desired trifluoromethyls. The acid group is fluorinated with sulfur tetrafluoride according to the process of Hasek et al., Chemistry of Sulfur Tetrafluoride, *J. Am. Chem. Soc.* 82, 543–551 (1960).

The following examples, showing the preparation of typical compounds of the invention, are presented to assure that organic chemists can easily obtain any desired compound. The products of the examples were identified by nuclear magnetic resonance analysis, elemental microanalysis, thin-layer chromatography, and in some instances, by mass spectrophotometry and infrared analysis.

EXAMPLE 1

N-methyl-2,4-dinitro-6-trifluoromethyldiphenylamine

A 27 g. portion of 2-chloro-3,5-dinitrobenzotrifluoride was added to 20 g. of aniline and 75 ml. of ethanol. After brief stirring at room temperature, the reaction mixture was seeded with a small sample of the desired intermediate product, and a precipitate formed immediately. The precipitate was separated by filtration and identified as 28.5 g. of 2,4-dinitro-6-trifluoromethyldiphenylamine.

The intermediate product was N-methylated in two different ways, both of which will be shown for the sake of clarity.

A. A 3.3 g. portion of the intermediate diphenylamine was taken up in 15 ml. of dimethylformamide, and 1.3 g. of sodium hydride was added. The mixture was stirred at room temperature, and 1.5 ml. of methyl iodide was added with the evolution of heat. After 1½ hours, another 2 ml. of methyl iodide was added, and the mixture was warmed slightly. After 2 hours more, the reaction mixture was added to a large amount of cold water, and the aqueous layer was decanted. The remaining oil was taken up in diethyl ether and stirred with magnesium sulfate and charcoal. After the solids were filtered away, the solution was evaporated to dryness to produce 2.4 g. of a dark red oil, which solidified upon cooling. The solid was heated with petroleum ether, cooled and filtered to produce 2.4 g. of N-methyl-2,4-dinitro-6-trifluoromethyldiphenylamine, m.p. 84°–86°.

|   | Theoretical | Found |
|---|---|---|
| C | 49.28% | 49.24% |
| H | 2.95 | 3.05 |
| N | 12.31 | 12.31 |

B. Eleven g. of the intermediate diphenylamine was combined with 45 ml. of dioxane, 14 g. of sodium carbonate and 6 ml. of dimethyl sulfate and stirred at reflux temperature for 24 hours. Twelve ml. of additional dimethyl sulfate and 10 g. of sodium carbonate were then added, and the mixture was stirred at reflux temperature for 2 hours more. It was then poured into water and stirred for 4 hours. The aqueous layer was then decanted and the residue was taken up in methylene chloride and filtered. The solute was identified as approximately 10 g. of crude N-methyl-2,4-dinitro-6-trifluoromethyldiphenylamine.

EXAMPLE 2

2,4-dinitro-N-propyl-6-trifluoromethyldiphenylamine

A 5 g. portion of the diphenylamine intermediate prepared in the first step of Example 1 was alkylated with propyl iodide in 80 ml. of dimethylformamide in the presence of 20 g. of sodium carbonate. The reaction mixture was stirred at 110° for 72 hours. The product was recovered by quenching the reaction mixture with water, extracting with methylene chloride, and evaporating the solvent under vacuum. Purification of the crude product on a silica gel chromatographic column, eluting with toluene, produced 1.2 g. of pure product, a liquid, NMR peaks at 0.93 (triplet), 1.35–2.05, 3.59, 6.45–6.78, 6.82–7.38, 8.63 and 8.76 ppm.

EXAMPLE 3

N-methyl-2,4-dinitro-2',6-bis(trifluoromethyl)diphenylamine

Following the general process of Example 1, 4.8 g. of 2-aminobenzotrifluoride was coupled with 8.1 g. of 2-chloro-3,5-dinitrobenzotrifluoride to produce 4.5 g. of 2,4-dinitro-2',6-bis(trifluoromethyl)diphenylamine, after purification over a silica gel column with methylene chloride as the eluting solvent.

A 2 g. portion of the above intermediate was alkylated with 5 ml. of dimethyl sulfate in acetone in the presence of sodium carbonate. The product was recrystallized from ethanol to produce 75 mg. of N-methyl-2,4-dinitro-2',6-bis(trifluoromethyl)diphenylamine, m.p. 148°–149° C.

|   | Theoretical | Found |
|---|---|---|
| C | 44.02% | 43.73% |
| H | 2.22 | 2.26 |
| N | 10.27 | 10.09 |

EXAMPLE 4

N,4-dimethyl-2',4'-dinitro-6'-trifluoromethyldiphenylamine

A 10 g. portion of p-toluidine was coupled with 12.6 g. of 2-chloro-3,5-dinitrobenzotrifluoride in ethanol according to the general process of Example 1. The intermediate product was recovered by filtration and identified as 10.1 g. of 4-methyl-2',4'-dinitro-6'-trifluoromethyldiphenylamine.

A 1 g. portion of the above intermediate was alkylated with 5 ml. of methyl iodide in 12 ml. of acetone in the presence of 5 g. of sodium carbonate. The mixture was stirred at reflux temperature for 96 hours. The mixture was then evaporated to dryness and the residue was digested with two 150-ml. portions of hot hexane. The hexane was filtered hot, and the filtrate was evaporated to dryness under vacuum. The residue was recrystallized from ethanol to produce 750 mg. of N,4-dimethyl-2',4'-dinitro-6'-trifluoromethyldiphenylamine, m.p. 124°–125°.

|   | Theoretical | Found |
|---|---|---|
| C | 50.71% | 50.51% |
| H | 3.40 | 3.35 |
| N | 11.83 | 11.75 |

EXAMPLE 5

N-methyl-2,4-dinitro-3',6-bis(trifluoromethyl)diphenylamine

Twenty g. of 3-aminobenzotrifluoride was coupled with 16.8 g. of 2-chloro-3,5-dinitrobenzotrifluoride in 200 ml. of anhydrous ethanol at reflux temperature overnight. The ethanol was then removed under vacuum and the product was separated from the hydrochloride salt byproduct by dissolving it in toluene. The toluene was then evaporated under vacuum and the intermediate product was recrystallized from ethanol to produce about 13 g. of 2,4-dinitro-3',6-bis(trifluoromethyl)diphenylamine, m.p. 99°–100°.

A 4 g. portion of the above intermediate was then alkylated with 10 ml. of dimethyl sulfate in acetone in the presence of sodium carbonate according to the process of Example 1B. The product was recrystallized from ethanol to collect 2 g. of N-methyl-2,4-dinitro-3',6-bis(trifluoromethyl)diphenylamine, m.p. 108°–109°.

|   | Theoretical | Found |
|---|---|---|
| C | 44.02% | 44.01% |
| H | 2.22 | 2.35 |
| N | 10.27 | 10.23 |

EXAMPLE 6

N,2-dimethyl-2',4'-dinitro-6'-trifluoromethyldiphenylamine

Fifteen g. of o-toluidine was coupled with 18.9 g. of 2-chloro-3,5-dinitrobenzotrifluoride in 150 ml. of ethanol at reflux temperature overnight. A precipitate formed when the mixture was cooled. The precipitate was collected and identified as 6.8 g. of 2-methyl-2',4'-dinitro-6'-trifluoromethyldiphenylamine.

The above intermediate was alkylated with 20 ml. of dimethyl sulfate in 25 ml. of acetone in the presence of 12 g. of sodium carbonate. The mixture was held at reflux temperature for 24 hours, and was then diluted with 50 ml. of water. The aqueous layer was decanted and the residue was taken up in methylene chloride, washed with water, filtered, and evaporated to dryness. The residue left after evaporating was purified by chromatography on a silica gel column with 1:1 pentane:methylene chloride as the eluting solvent. Four g. of pure N,2-dimethyl-2',4'-dinitro-6'-trifluoromethyldiphenylamine, m.p. 106°–108°, was collected.

|   | Theoretical | Found |
|---|---|---|
| C | 50.71% | 50.88% |
| H | 3.40 | 3.46 |
| N | 11.83 | 12.08 |

The intermediates of this invention are used in the preparation of an important series of rodenticides of the formula

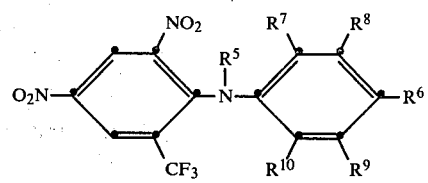

wherein $R^5$ represents methyl, ethyl or propyl;

$R^6$ represents hydrogen, fluoro, chloro, bromo, iodo or methyl;

$R^7$ and $R^{10}$ independently represent hydrogen, fluoro, chloro, bromo, nitro, methyl or trifluoromethyl, provided that no more than one of $R^7$ and $R^{10}$ represents nitro;

$R^8$ and $R^9$ independently represent hydrogen, methyl, fluoro, chloro, bromo or trifluoromethyl; provided that (a) no more than one of $R^6$, $R^7$, $R^8$, $R^9$ and $R^{10}$ represents methyl, except that $R^8$ and $R^9$ may both represent methyl;

(b) when $R^6$, $R^7$, $R^8$, $R^9$ or $R^{10}$ represents methyl or fluoro, two or three of $R^6$, $R^7$ and $R^{10}$ represent chloro or bromo;

(c) no more than one of $R^7$, $R^8$, $R^9$ and $R^{10}$ represents trifluoromethyl, except that $R^8$ and $R^9$ may both represent trifluoromethyl;

(d) when $R^7$ or $R^{10}$ represents trifluoromethyl, $R^6$ represents chloro or bromo;

(e) when one and only one of $R^8$ and $R^9$ represents trifluoromethyl, two or three of $R^6$, $R^7$ and $R^{10}$ represent chloro or bromo;

(f) no more than four of $R^6$, $R^7$, $R^8$, $R^9$ and $R^{10}$ represent hydrogen;

(g) two fluorine atoms are not adjacent to each other;

(h) when $R^7$ or $R^{10}$ represents nitro, $R^6$ represents chloro, bromo or nitro;

(i) when $R^7$, $R^8$, $R^9$ or $R^{10}$ represents trifluoromethyl, none of $R^6$, $R^7$, $R^8$, $R^9$ and $R^{10}$ represents fluoro or methyl.

The intermediates of this invention are converted to the above rodenticides by halogenating or nitrating the aniline ring appropriately. The reactions follow the usual practice of organic chemistry.

For example, halogenations are usually best performed with the elemental halogen in acetic acid, or in methylene chloride or the like halogenated solvent, including chloroform or carbon tetrachloride. Room temperature halogenation is usually effective, but increased speed of reaction is obtainable by slight elevation of the reaction temperature in the range of 25°–50°. Chlorination is best done with the elemental gaseous halogen, but bromination may be done with such agents as N-bromosuccinimide and dibromoisocyanuric acid, although reaction with elemental bromine is usually quite satisfactory.

Iodination is best carried out with iodine monochloride as the reagent. Such iodinations are discussed, for example, by Ginsberg, *J. Am. Chem. Soc.* 75, 1107 (1953), and by Johnson et al., *Org. Syn.*, Coll. Vol. 2, 343 (1943).

When a compound having no 4-substituent is to be made, it will often be necessary to block the 4-position before halogenating. It is most convenient to use a sulfonic acid as the blocking group, because it is readily added and readily removed. See, for example, Sandler and Karo, Organic Functional Group Preparations, 506-24 (Academic Press 1968); and Wagner and Zook, Synthetic Organic Chemistry 15 (Wiley 1953).

Insertion of nitro groups on the aniline ring is readily accomplished with concentrated nitric acid in acetic acid solution at room temperature. Other nitration reactions may also be used, such as a mixture of concentrated nitric and sulfuric acids at elevated temperatures. In general, no solvent is used in nitration reactions other than the acids themselves.

While synthesis of the rodenticides from the intermediates of this invention is believed to be readily understandable, a few examples will be shown to assure that organic chemists can prepare any desired rodenticide of the above group.

Preparation 1

2,4-dibromo-N-methyl-2',4'-dinitro-6'-trifluoromethyldiphenylamine

The crude N-methyl-2,4-dinitro-6-trifluoromethyldiphenylamine obtained from paragraph B of Example 1 above was brominated without further purification by the addition of excess elemental bromine to the methylene chloride solution. The reaction mixture was stirred for 1 hour, and was then washed, first with water and then with sodium bisulfite solution. The organic solution was then filtered and evaporated to dryness, and the residue was recrystallized from ethanol to obtain 11 g. of 2,4-dibromo-N-methyl-2',4'-dinitro-6'-trifluoromethyldiphenylamine, m.p. 110°.

|   | Theoretical | Found |
|---|---|---|
| C | 33.70% | 33.95% |
| H | 1.62 | 1.86 |
| N | 8.42 | 8.52 |

Preparation 2

2,4-dibromo-6-chloro-N-methyl-2',4'-dinitro-6'-trifluoromethyldiphenylamine

A 2.5 g. portion of the product of Preparation 1 was dissolved in 10 ml. of methylene chloride, and the solution was saturated with elemental gaseous chlorine. After standing for 2 hours, the solution was evaporated to dryness under vacuum and the residue was recrystallized from ethanol to produce 2.1 g. of product, m.p. 139°-141°.

|   | Theoretical | Found |
|---|---|---|
| C | 31.52% | 31.78% |
| H | 1.32 | 1.35 |
| N | 7.88 | 8.10 |

Preparation 3

2,4,6-tribromo-N-methyl-2',4'-dinitro-6'-trifluoromethyldiphenylamine

A 2.5 g. portion of the product of Preparation 1 was dissolved in 25 ml. of diethyl ether and 1.5 ml. of concentrated sulfuric acid. The mixture was stirred at room temperature while 0.7 g. of dibromoisocyanuric acid was added. After 30 minutes of stirring, another 0.7 g. of dibromoisocyanuric acid and 1.5 ml. of sulfuric acid were added, and the addition was repeated again after another 15 minutes of stirring. Five minutes after the last addition, the reaction mixture was diluted with 50 ml. of diethyl ether and filtered. The organic layer was washed three times with 10 percent sodium carbonate solution, dried over magnesium sulfate and evaporated to dryness. The residue was recrystallized from ethanol to produce 2.4 g. of 2,4,6-tribromo-N-methyl-2',4'-dinitro-6'-trifluoromethyldiphenylamine, m.p. 150°-151°.

|   | Theoretical | Found |
|---|---|---|
| C | 29.10% | 29.02% |
| H | 1.22 | 1.06 |
| N | 7.27 | 7.29 |

Preparation 4

2,4,6-trichloro-2',4'-dinitro-N-propyl-6'-trifluoromethyldiphenylamine

A 1.2 g. portion of the product of Example 2 above was dissolved in acetic acid, and the solution was saturated with chlorine and stirred at reflux for 4 hours. The product was purified by quenching the mixture in water, extracting with methylene chloride, washing the extract with sodium bicarbonate solution and then with water, and finally chromatographing on a silica gel column with pentane:toluene, 5:1. The yield was 0.35 g. of 2,4,6-trichloro-2',4'-dinitro-N-propyl-6'-trifluoromethyldiphenylamine, an oily liquid.

|   | Theoretical | Found |
|---|---|---|
| C | 40.66% | 40.66% |
| H | 2.35 | 2.22 |
| N | 8.89 | 8.71 |
| Cl | 22.50 | 22.45 |

The $R^1$ or $R^2$=trifluoromethyl compounds of this invention, especially the N-alkyl-2,4-dinitro-3',6-bis(trifluoromethyl)diphenylamines, are additionally useful as insecticides and arachnicides. The compounds can be used to control insects and arachnids, especially mites which attack plants and stored foods. The compounds control numerous mite species, such as the two-spotted spider mite (*Tetranychus urticae*), when applied to the foliage of infested plants in liquid formulations containing from 10 to 5000 ppm of compound, and preferably from 500 to 1500 ppm of compound. The compounds exhibit activity against both adults and eggs. The compounds surprisingly exhibit little or no phytotoxicity.

It is believed that compounds of the present invention can be synthesized by an alternate method which in some instances may be preferred to the methods described above. In this synthetic route a fluorobenzene is condensed with an N-alkylaniline, yielding the desired N-alkyldiphenylamine directly:

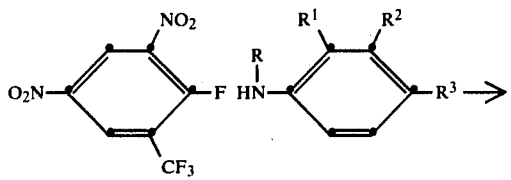

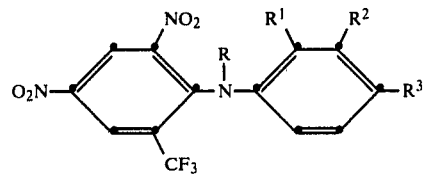

Furthermore, the fluorobenzene can be prepared in situ from the corresponding chlorobenzene,

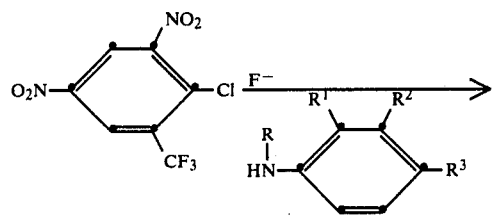

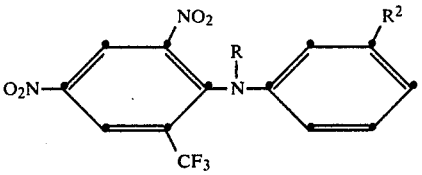

To date, the preferred source of fluoride is potassium fluoride, the preferred solvent is DMSO, and suitable reaction temperatures are 50°–100° C.

We claim:

1. A compound of the formula wherein R represents methyl, ethyl, or propyl; and $R^2$ represents trifluoromethyl.

2. The compound of claim 1 which is N-methyl-2,4-dinitro-3',6-bis(trifluoromethyl)diphenylamine.

3. The compound of claim 1 which is 2,4-dinitro-N-propyl-3',6-bis(trifluoromethyl)diphenylamine.

* * * * *